United States Patent [19]

Bremer et al.

[11] 4,178,793
[45] Dec. 18, 1979

[54] APPARATUS FOR OXYGEN SENSOR IMPEDANCE MEASUREMENT

[75] Inventors: Richard J. Bremer, Grand Blanc; Daniel J. Richardson, Swartz Creek, both of Mich.

[73] Assignee: General Motors Corporation, Detroit, Mich.

[21] Appl. No.: 939,465

[22] Filed: Sep. 5, 1978

[51] Int. Cl.$^2$ ............................................ G01N 27/46
[52] U.S. Cl. .................................. 73/23; 123/32 EE; 123/119 EC
[58] Field of Search ............... 73/23; 204/195 S, 1 T; 123/32 EE, 119 EC; 60/276; 307/358

[56] References Cited

U.S. PATENT DOCUMENTS

| | | | |
|---|---|---|---|
| 3,616,274 | 10/1971 | Eddy | 204/195 S |
| 3,938,479 | 2/1976 | Oberstadt | 123/32 EA |
| 4,094,186 | 6/1978 | Wessel | 73/23 |
| 4,106,450 | 8/1978 | Norimatsu et al. | 123/119 EC |
| 4,120,269 | 10/1978 | Fujishiro | 123/32 EE |
| 4,135,381 | 1/1979 | Sherwin | 73/23 |

OTHER PUBLICATIONS

"Lambda-Sensor with Y$_2$O$_3$ Stabilized ZrO$_2$ Ceramic for Application in Automotive Emission Control Systems", SAE Paper 770401, pp. 53-58.

*Primary Examiner*—Stephen A. Kreitman
*Attorney, Agent, or Firm*—Robert M. Sigler

[57] ABSTRACT

A vehicle engine exhaust mounted oxygen sensor of the type producing an internally generated signal voltage and having a variable internal impedance is connected in series with a reference impedance and a semiconductor switch, the semiconductor switch having an impedance which may become large when current therethrough is very low. A constant current source is connected to supply current to the junction of the sensor and reference impedance at one sensor terminal and thus guarantee a minimum current and small switch impedance when the sensor impedance is large. Further apparatus samples the magnitudes of the voltage at the one sensor terminal with the semiconductor switch in its conducting and non-conducting states, the ratio of said magnitudes varying with sensor impedance. The ratio can be compared with one or more references to provide a warm sensor signal or control the operation of a sensor heater.

1 Claim, 4 Drawing Figures

APPARATUS FOR OXYGEN SENSOR IMPEDANCE MEASUREMENT

BACKGROUND OF THE INVENTION

This invention relates to vehicle exhaust mounted oxygen sensors of the solid electrolyte type and particularly to apparatus for measuring the internal impedance thereof during operation of the vehicle engine.

Oxygen sensors of the solid electrolyte type are used with vehicle mounted internal combustion engines as exhaust mounted sensors for providing an air-fuel ratio signal to the engine fuel supply apparatus in order to maintain maximum efficiency in a three-way catalytic converter, which requires the air-fuel ratio to be kept within very narrow limits. A sensor of this type normally contains a solid electrolyte cell which is effective to generate internally, in response to the composition of the exhaust gases to which it is exposed, an electrical voltage signal across a pair of output terminals. When the sensor becomes sufficiently warm, the voltage across the output terminals tends to vary only a little from a typical value of 100 millivolts when the air-fuel ratio is lean and a typical value of 900 millivolts when the air-fuel ratio is rich and to change rather sharply between 100 and 900 millivolts in a narrow region around stoichiometry.

The temperature of such sensors has a great effect upon their performance characteristics. For instance, a sensor at a temperature far below the "warm sensor" temperature has an extremely high internal impedance and thus a voltage across its output terminals determined by any external voltage source connected across the terminals. In addition, even at temperatures above the "warm sensor" temperature, such sensors often exhibits a change in slope with temperature in the output voltage curve within the fast changing region about stoichiometry which results, in the dynamic operation of a closed loop fuel control system, in a sensor response time which correspondingly decreases with increasing temperature.

In addition, the hostile environment of the hot, corrosive and fast flowing exhaust gases causes wear on the portion of the sensor exposed to such gases, which wear may result over time in an increase in the response time of the sensor at a given temperature, as well as an increase in the internal impedance of the sensor at that temperature. It has been found that restoration of the internal impedance of the sensor to the original internal impedance of the sensor when new, such as by using heating means to increase the temperature of the sensor until the desired internal impedance is reached, may have the beneficial result of restoring the original response time. Thus, the internal impedance of such a sensor is found to be a good indication of sensor temperature in the short run and of sensor response time in the long run. It would therefore be advantageous in many closed loop fuel control systems using such sensors to provide apparatus for measuring the internal impedance of an oxygen sensor without interfering in the control of the fuel system by the sensor.

A well known technique for measuring the internal impedance of a battery cell involves the steps of first measuring the output voltage of the unloaded cell and next measuring the output voltage of the cell when loaded by a known test impedance. The ratio of said measured voltages varies with the internal impedance of the cell, showing a very small value when the cell internal impedance is large and a value increasing toward one as the cell internal impedance becomes smaller. In order to apply this technique to the case of an oxygen sensor in a vehicle engine closed loop fuel control system, switching means must be provided for automatically switching an internal impedance into and out of a series circuit relationship with the oxygen sensor. For the practical reasons of size, cost and reliability, such switch apparatus is preferably in the form of a semiconductor switch in an electronic circuit.

There is a problem, however, with using a semiconductor switch in such a circuit with a typical oxygen sensor. A semiconductor switch is characterized when conducting by an impedance which may increase greatly at very small conduction currents. When the sensor is warm, there is generally sufficient voltage generated across the sensor terminals to produce a current through the test impedance and switch large enough that the test impedance predominates. However, a cold sensor generates a very small voltage across its terminals, due to the high internal impedance, and thus generates very little current through the test impedance and switch. The switch impedance may thus become large enough to significantly affect the measured voltage across the sensor terminals and change the desired relationship between the loaded-unloaded sensor voltage difference and sensor impedance.

SUMMARY OF THE INVENTION

This invention provides apparatus for measuring the internal impedance of a vehicle engine exhaust mounted oxygen sensor which is not encumbered by the aforementioned difficulty and which reliably produces a signal which varies with said internal impedance. A known test impedance is connected to one terminal of the sensor and in series with the sensor and a semiconductor switch. In addition, a constant current source is connected to supply current to the junction of the one sensor terminal and the test impedance, to guarantee at least a predetermined minimum current flow through the test impedance when the semiconductor switch is conducting. Further apparatus is provided for measuring and storing the voltage at the one sensor terminal with the semiconductor switch not conducting, measuring the voltage at the one sensor terminal with the semiconductor switch conducting and comparing this latter voltage with the stored voltage to provide an output difference signal. The constant current source provides a dependable current through the test impedance when the semiconductor switch is closed but does not significantly affect the unloaded output voltage signal of the sensor, which is provided to the closed loop fuel control system. The ratio of loaded to unloaded sensor output voltage is therefore indicative of sensor internal impedance and may be compared with a reference to provide a warm-cold sensor signal or an on-off signal to sensor heater control means. The stored voltage is available for application to the closed loop fuel control system on a time sampled basis.

Further details and advantages of this invention will be apparent from the accompanying drawings and following description of a preferred embodiment.

DESCRIPTION OF THE PREFERRED EMBODIMENT

Figure 1:
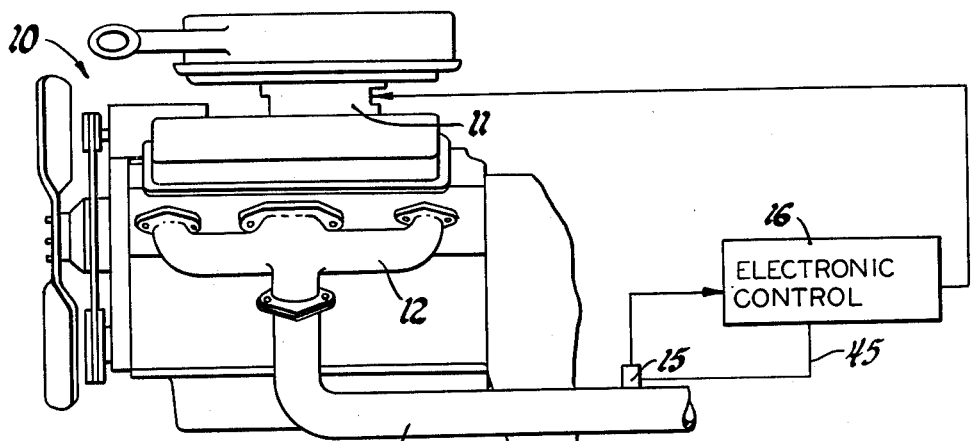
FIG. 1 shows a motor vehicle engine providing an environment for this invention.

Referring to FIG. 1, a vehicle mounted internal combustion engine 10 includes air and fuel delivery means 11, which mix air and fuel in a controllable ratio and supply the mixture as demanded to engine 10. Air and fuel delivery means 11, hereinafter called fuel delivery means 11, can be a carburetor with controllable metering rod, manifold or throttle body fuel injection means or any other fuel system that allows control over air-fuel ratio.

Engine 10 further includes an exhaust manifold 12 and an exhaust conduit 14 for conducting exhaust gases from engine 10. An oxygen sensor 15 is mounted in exhaust conduit 14 in such a way that an active cell surface is exposed to the exhaust gas soon after it leaves engine 10. The output of oxygen sensor 15 is supplied to an electronic control unit or ECU 16, which generates a signal to control the air-fuel ratio of fuel delivery means 11, either directly or through a vacuum modulation system.

Figure 2:
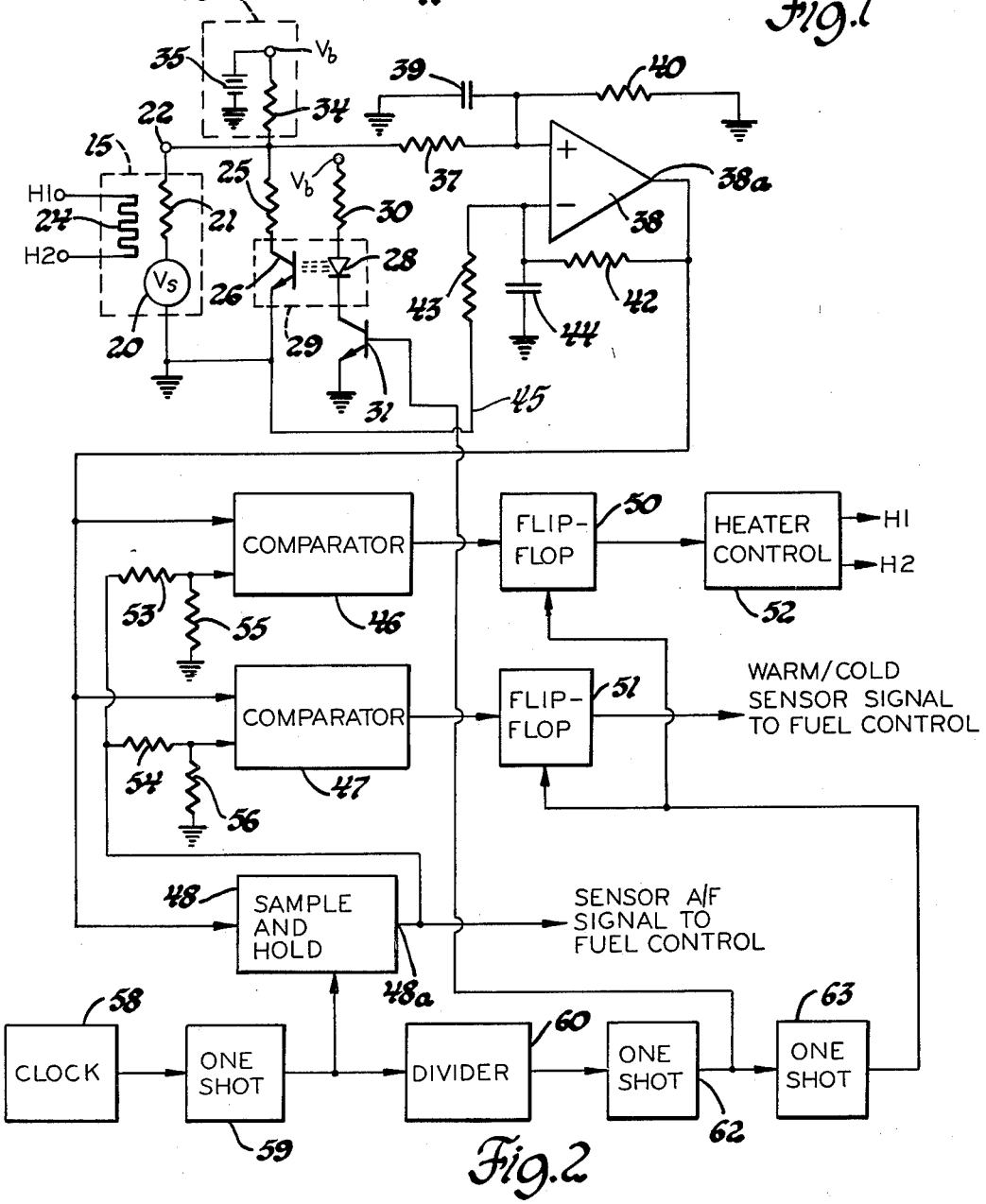
FIG. 2 shows a partial circuit and partial block diagram of oxygen sensor impedance measuring apparatus according to this invention for use in the engine of FIG. 1.

FIG. 2 shows, in more detail, oxygen sensor 15 and a portion of electronic control 16. Sensor 15 is represented by an internal voltage source 20 in series with an internal impedance 21. Internal voltage source 20 is labeled Vs in FIG. 2 and is distinguished from the voltage that appears across the terminals of the sensor, one of which terminals is grounded to the vehicle exhaust conduit 14 and the other of which is identified as terminal 22. The internally generated voltage Vs represents the internally generated voltage due to the solid electrolyte cell, which depends at least on the partial pressure of oxygen in the exhaust gases in conduit 14 compared with that in the atmosphere outside conduit 14. Internal impedance 21 is the equivalent internal impedance as measured between the sensor output terminals and varies greatly with the temperature of sensor 15. Sensor 15 may also be provided with a heater element 24 of the electrical resistance type having terminals labeled H1 and H2. Heater element 24 may be incorporated physically into sensor 15 or otherwise supported in proximity to sensor 15 so that the heat generated thereby is effective to raise the temperature of sensor 15 and thus lower its internal impedance 21.

A test impedance, in the form of a resistor 25, has one end connected to terminal 22 of sensor 15 and the other connected through a semiconductor switch 26 to the grounded terminal of sensor 15. In this embodiment, semiconductor switch 26 has a light-sensitive gate and is packaged with a light emitting diode 28 in an optical isolation switch package 29. A source of constant electrical potential Vb, to be further described below, is connected through a resistor 30, diode 28 and the collector and emitter of a transistor 31 to ECU ground. Transistor 31 is operated as a switch to control current through diode 28 and therefore switch semiconductor switch 26 between a conducting and a nonconducting state.

In order to insure conduction through semiconductor switch 26 when it is switched into its conducting state, the source of constant potential Vb is connected through a bias resistor 34 to terminal 22 of sensor 15 and thus in series with resistor 25 and semiconductor switch 26. Potential source Vb, identified in FIG. 2 as a battery 35, supplies electric current at a substantially constant potential of typically 6 volts or greater, which is much larger than the semiconductor switch voltage drop or the sensor output voltage. In addition, the resistance of resistor 34 is very high, such as 5 megohms, so that the combination of battery 35 and resistor 34 acts as a constant current source, identified with reference numeral 36, in this circuit. Battery 35 may be the normal vehicle battery and alternator, suitably regulated.

Terminal 22 of sensor 15 is connected through a resistor 37 to the noninverting input of an operational amplifier 38, which input is also connected through a capacitor 39 and resistor 40 in parallel to ECU ground. Besides providing the correct zero level for amplifier 38, resistors 37 and 40 provide a current path to ground for constant current source 36 when semiconductor switch 26 is not conducting. The voltage at the sensor output terminal 22 under this condition is set by a voltage divider comprising resistors 34, 37 and 40 to a value, such as 350 millivolts, between the maximum and minimum normal sensor output voltages to avoid problems with the sensor from too high a voltage being impressed thereon.

The output of amplifier 38 is connected through a feedback resistor 42 to the inverting input, which is also connected through a resistor 43 to the grounded side of sensor 15 and through a capacitor 44 to ECU ground. The connection of resistor 43 and semiconductor switch 26 to the grounded terminal of sensor 15 is preferably through a separate wire 45 and not through the ECU and vehicle grounds. This guarantees a common reference for the devices. The output of amplifier 38 is further connected to one input of a comparator 46, one input of a comparator 47 and the sample input of a sample and hold circuit 48. The outputs of comparators 46 and 47 are connected, respectively, to the sample inputs of flip-flops 50 and 51. These comparator and flip-flop arrangements are shown in more detail in FIG. 3, which will be described at a later point in this specification. The output of flip-flop 50 switches a heater controller 52, which supplies, when switched on, a regulated heating current to terminals H1 and H2 of heater element 24. The output of flip-flop 51 may be provided as a warm/cold sensor signal to another part of electronic control 16, not shown, to switch the control means from an open loop mode to a closed loop mode when the sensor becomes warm enough to generate a reliable output.

The output of sample and hold circuit 48 is supplied as the sensor air-fuel signal to the closed loop fuel control portion of electronic control 16 and is further connected through resistors 53 and 54, respectively, to the other inputs of comparators 46 and 47, which other inputs are also connected through resistors 55 and 56 to ground.

Timing means are provided for the system of FIG. 2 in the form of a clock 58, which can be any suitable oscillator which generates regular clock pulses and supplies them to a one shot 59, which is thereby caused to output pulses of predetermined width at the clock rate to the trigger input of sample and hold circuit 48 to cause a sampling of the output of amplifier 38 for the duration of each pulse. The output of one shot 59 is also provided through a divider 60 to a one shot 62. One shot 62 is designed to trigger on the trailing edge of the pulses from divider 60 and is thus effective to generator a pulse of predetermined width following each Nth pulse from one shot 59, where N is the divide ratio of divider 60. The output of one shot 62 is connected to the base of transistor 31 to control semiconductor switch 26 and is further connected to a one shot 63 which produces a pulse during each pulse of one shot 62 but shorter in duration and supplies these pulses to the trigger inputs of flip-flops 50 and 51.

Figure 3:
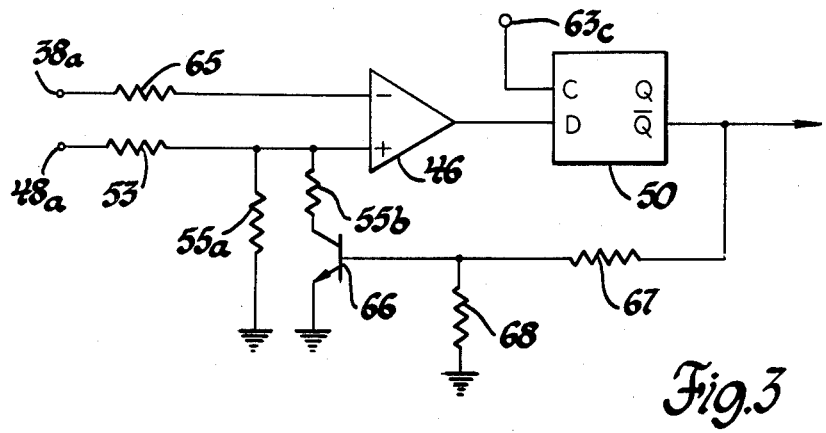
FIG. 3 shows a circuit diagram of a voltage comparator and flip-flop combination for use in the apparatus of FIG. 2.

FIG. 3 shows the interconnection between comparator 46 and flip-flop 50 and thereby, by analogy, between comparator 47 and flip-flop 51, which is substantially identical. Comparator 46 has its inverting input connected through a resistor 65 to the output of amplifier 38, which is indicated in FIG. 3 as a terminal 38a. The noninverting input of comparator 46 is connected through resistor 53 to the output of sample and hold circuit 48, which is indicated in this figure by terminal 48a, and is further connected to ground through a resistor 55a and, in parallel, through a resistor 55b in series with the collector and emitter of a transistor 66. Resistors 55a and 55b together comprise the resistor 55 shown in FIG. 2, which resistor 55 has the resistance of resistor 55a alone when transistor 66 is in its nonconducting state and has the combined parallel resistance of resistors 55a and 55b when transistor 66 is in its conducting state. Resistors 53 and 55 forms a voltage divider between the output of sample and hold circuit 48 and ground for the noninverting input of comparator 46, which voltage divider provides a first division ratio when transistor 66 is conducting and a second division ratio when transistor 66 is not conducting.

Flip-flop 50 is a standard D type flip-flop in which clock pulses provided to clock input C cause the $\bar{Q}$ output to assume the opposite logical condition from the D input. Flip-flop 50 has its D input connected to the output of comparator 46 and its C input connected to the output of one shot 63, which is shown in this figure as terminal 63c. The $\bar{Q}$ output of flip-flop 50, besides being connected to heater control 52 as shown in FIG. 2, is connected through a resistor 67 to the base of transistor 66, which is also connected through a resistor 68 to ground.

In the operation of the circuit of FIG. 3, when the voltage applied to the inverting input of comparator 46 exceeds the voltage applied to the noninverting input, the output switches low; and the next clock input to flip-flop 50 causes the $\bar{Q}$ output to switch high. This causes transistor 66 to switch to a conducting state and connect resistor 55b in parallel with resistor 55a to reduce the voltage applied to the noninverting input of comparator 46. If the voltage applied to the inverting input of comparator 46 should decrease, it must decrease to a new, lower level before the comparator switches to a high output. A clock input to flip-flop 50 then causes the $\bar{Q}$ output to switch low and turn off transistor 66, thus removing resistor 55b from the circuit and causing the voltage on the noninverting input of comparator 46 to once again rise to its original level. If the voltage applied to the inverting input of comparator 46 should rise again, it must rise to the original switching level before the output of comparator 46 will once again switch low. Thus, the circuit provides hysteresis in the switching of comparator 46 for stability in the system.

Figure 4:
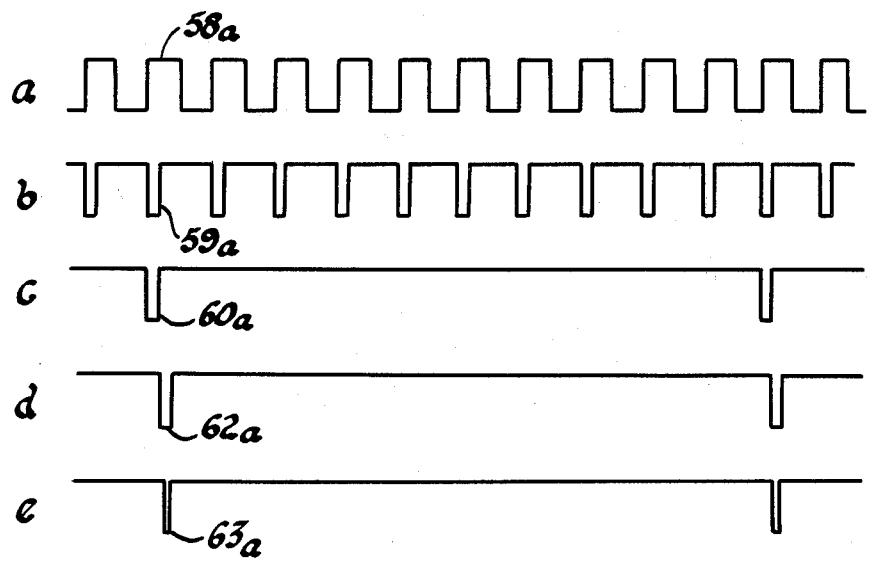
FIG. 4 shows a series of timing diagrams illustrating the operation of the apparatus of FIG. 2.

The timing of the system will now be described, with reference to FIG. 2 and the timing diagrams of FIG. 4. The output of clock 58 is shown as wave form 58a in FIG. 4a. A typical clock rate for the pulses from clock 58 is 100 hertz, which results in a pulse every 10 milliseconds, the width of the pulses being unimportant. The output of one shot 59 is shown as wave form 59a of FIG. 4b. There is one pulse of wave form 59a, having a typical width of one millisecond, for every pulse of wave form 58a. Each pulse from one shot 59 causes the sample and hold circuit 48 to sample the output of amplifier 38 for the one millisecond duration of the pulse, the value obtained being stored in sample and hold circuit 48 and made available at the output thereof until the next sampling pulse from one shot 59. This sampled value is an analog of the unloaded sensor output voltage and is available as a sensor air-fuel ratio signal to the closed loop fuel control as well as to comparators 46 and 47.

The 100 hertz clock rate is determined by the requirement of the fuel control apparatus 11 for the frequency of update on the sensor output voltage, since this is basically a sensor sampling system. However, it is not necessary for either the warm/cold sensor determination or the sensor heater control that the sensor internal impedance be tested at this rate. In fact, for the heater control, it is desirable that the sensor internal impedance be tested at a slower rate to achieve greater accuracy and stability in the closed loop impedance control loop. Therefore, the output of divider 60, which is shown as wave form 60a in FIG. 4c, comprises one pulse for every 10 pulses from one shot 59. Each of the pulses from divider 60 generates a trailing pulse from one shot 62, the output of which is shown as wave form 62a in FIG. 4d. Each of these pulses from one shot 62 gates transistor 31 on to cause conduction through light emitting diode 28 and gate the semiconductor switch 26 into its conducting state. Sensor 15 is thus loaded through test impedance 25 for the duration of each pulse from one shot 62.

During each pulse from one shot 62, therefore, comparator 46 sees, through resistor 65, a voltage proportional to the unloaded sensor output voltage on one input thereof and, through the voltage divider of resistors 53 and 55, a voltage proportional to the loaded sensor output voltage from amplifier 38 on the other input thereof. Comparator 47 has a similar set of inputs; and the resistors for each of the comparators are chosen such that the output of the comparator will switch between a low and high output at a particular sensor internal impedance, which can be set at a different level for each of the comparators 46 and 47. For example, comparator 46 might be designed to switch from a high output to a low output when the sensor internal impedance falls below 100 ohms and to switch from a low output to a high output as the sensor internal impedance rises above 200 ohms, thus causing the heater to maintain a low sensor internal impedance with a high degree of hysteresis. Comparator 47, on the other hand, could be designed to switch between its high and low outputs at appropriate values of sensor internal impedance near 2,000 ohms. Thus, as engine 10 is started, sensor 15 warms up and the internal impedance 21 of sensor 15 falls, the warm sensor signal would be sent from flip-flop 51 when the sensor impedance fell below 2,000 ohms, but the heater control 52 would remain switched on until the sensor impedance fell to the 100 ohm level. During normal operation of the engine, then, the sensor impedance would be maintained between 100 and 200 ohms, not only to guarantee that the sensor temperature remained in the active range, but also to maintain sensor response time within a desired range throughout the life of the sensor.

The output of one shot 63 is shown as wave form 63a in FIG. 4e and comprises a pulse of duration of approximately 500 to 750 microseconds occurring during the one millisecond wide pulse of wave form 62a. The pulses from one shot 63 thus cause flip-flops 50 and 51 to update their outputs in response to their inputs from comparators 46 and 47.

Finally, the operation of the sensor and biasing circuit will be described. The sensor internal impedance 21 is capable, over the short run, of assuming an extremely wide range of values and is highly dependent upon temperature. For example, this impedance might be 100 to 200 ohms at a typical high engine exhaust temperature but may rise to several megohms at normal atmospheric temperatures. The test impedance 25 will determine an impedance range where the accuracy of the impedance measurement is greatest. Since, in this embodiment, impedance values of 100 to 2,000 ohms are desired, a value of 510 ohms is appropriate. Biasing impedance 34 can be, as mentioned before, 5.1 megohms; while resistors 37 and 40 are each 100 kilohms.

When the sensor is cold and the sensor impedance 21 is thus high in comparison with test impedance 25, there is an unloaded voltage on terminal 22, determined by voltage Vb supplied through the voltage divider comprising resistors 34, 37 and 40, of typically 350 millivolts. The loaded voltage, however, is essentially the voltage drop of the conducting semiconductor switch 26 or, typically, 70 millivolts for a ratio of loaded to unloaded voltage equaling one fifth.

As the sensor warms and the internal impedance 21 drops, the ratio of the loaded to the unloaded voltage at terminal 22 increases toward a limit of 1, since, for very small values of resistor 21, the voltage at terminal 22 varies little from Vs whether semiconductor switch 26 is conducting or not. It should be apparent that the arrangement of providing the unloaded voltage to one input of comparator 46 while providing a fraction of the loaded voltage to the other input of comparator 46 results in the comparison of the ratio of the loaded and unloaded voltages to a reference determined by the aforementioned fraction. It should also be noted that, at sensor impedances for which the closed loop fuel control is activated and an accurate sensor output voltage is therefore required (2,000 ohms or lower in this embodiment), this output voltage will not be affected significantly by voltage Vb, due to the large resistance of resistor 34. For a very cold sensor, whose impedance may approach the resistance of resistor 34, the sensor output is ignored, so any inaccuracy introduced by voltage Vb would be irrelevant.

Thus, this system presents circuitry to guarantee a sufficient current through a semiconductor switch 26 for measurement of the loaded sensor voltage at terminal 22 but does not adversely affect the measurement of the unloaded voltage at sensor 22 over the range of sensor internal impedances for which a sensor output signal is desired in the operation of engine 10. This permits a closed loop control of sensor internal impedance by means of a heater which not only warms up the sensor more quickly in the short run but also may help maintain sensor response time within acceptable limits for the life of the sensor, in spite of sensor wear due to corrosive exhaust gases. It also permits determination of closed versus open loop control modes for the fuel control of engine 10. Many variations of the apparatus shown herein are possible within the scope of this invention; and, therefore, this invention should be limited only by the scope of the claim which follow.

The embodiments of the invention in which an exclusive property or privilege is claimed are defined as follows:

1. In combination with a vehicle engine exhaust mounted oxygen sensor of the type having a pair of output terminals with a variable internal impedance across said terminals and being effective to generate an output signal voltage across said terminals, apparatus for measuring said internal impedance, comprising:

a test impedance;

a semiconductor switch connected in series with said sensor and said test impedance, the semiconductor switch being characterized by an internal impedance which may increase greatly with low current therethrough;

a constant current source connected to supply a constant electrical current to the one sensor terminal, said constant current source being effective to provide current through the reference impedance and semiconductor switch when the sensor internal impedance becomes large;

first means effective to sense and store the magnitude of the voltage at the one sensor terminal with the semiconductor switch not conducting;

second means effective to sense the magnitude of the voltage at the one sensor terminal with the semiconductor switch conducting for comparison with the magnitude stored in the first means, the ratio of said magnitudes varying with and thus indicating said sensor impedance.

* * * * *